(12) United States Patent
Kozersky

(10) Patent No.: US 9,504,596 B1
(45) Date of Patent: Nov. 29, 2016

(54) CONVERTIBLE ORTHOTIC BRACE

(71) Applicant: Capital Prosthetic & Orthotic Center, Inc., Columbus, OH (US)

(72) Inventor: David J. Kozersky, Columbus, OH (US)

(73) Assignee: Capital Prosthetic and Orthotic Center, Inc., Columbus, OH (US)

( * ) Notice: Subject to any disclaimer, the term of this patent is extended or adjusted under 35 U.S.C. 154(b) by 0 days.

(21) Appl. No.: 14/696,017

(22) Filed: Apr. 24, 2015

Related U.S. Application Data

(63) Continuation-in-part of application No. 14/312,357, filed on Jun. 23, 2014, which is a continuation of application No. 13/492,363, filed on Jun. 8, 2012, now Pat. No. 8,758,284.

(60) Provisional application No. 61/983,950, filed on Apr. 24, 2014.

(51) Int. Cl.
*A61F 5/00* (2006.01)
*A61F 5/02* (2006.01)

(52) U.S. Cl.
CPC .............. *A61F 5/028* (2013.01); *A61F 5/026* (2013.01)

(58) Field of Classification Search
CPC .......... A61F 5/028; A61F 5/024; A61F 5/02; A61F 5/30; A61F 2250/001; A61F 5/022; A61F 5/026; A61F 5/34; A61F 5/03; A61F 5/012; A61F 2/30942; A61F 5/01; A61F 5/32; A61F 5/3776; A61F 5/3784
USPC .................................................... 602/17–19
See application file for complete search history.

(56) References Cited

U.S. PATENT DOCUMENTS

| | | | | |
|---|---|---|---|---|
| 5,362,304 A * | 11/1994 | Varn | ...................... | A61F 5/028 2/44 |
| 6,676,620 B2 * | 1/2004 | Schwenn | ................ | A61F 5/028 128/96.1 |
| 6,899,689 B1 * | 5/2005 | Modglin | ................. | A61F 5/022 128/869 |
| 7,316,660 B1 * | 1/2008 | Modglin | ................. | A61F 5/024 602/19 |
| 2013/0006158 A1 * | 1/2013 | Ingimundarson | ....... | A61F 5/028 602/19 |
| 2014/0155798 A1 * | 6/2014 | Ingimundarson | ....... | A61F 5/024 602/19 |

* cited by examiner

*Primary Examiner* — Michael Brown
(74) *Attorney, Agent, or Firm* — Ice Miller LLP

(57) ABSTRACT

A lumbar-sacral orthosis comprises in combination a first lateral belt portion having a dorsal end portion having two substantially parallel horizontally extending upper and lower slots, the first lateral belt portion having a third slot, a second lateral belt portion having a dorsal end portion having two substantially parallel horizontally extending upper and lower slots, the first lateral belt portion substantially parallel horizontally extending upper and lower slots and the second lateral belt portion substantially parallel horizontally extending upper and lower slots being substantially aligned, a central dorsal portion, the central dorsal portion attached to the first and second lateral belt portions by an upper pin extending from the central dorsal portion through the upper slots, and a lower pin extending from the central dorsal portion through the lower slots, such that the first and second lateral belt portions may be moved with respect to one another.

36 Claims, 21 Drawing Sheets

CONVERTIBLE ORTHOTIC BRACE

RELATED APPLICATION DATA

This application is a continuation-in-part of U.S. patent application Ser. No. 14/312,357, filed Jun. 23, 2014, which is a continuation of U.S. patent application Ser. No. 13/492,363, filed Jun. 8, 2012, and claims the benefit of U.S. Patent Application Ser. No. 61/983,950, filed Apr. 24, 2014, which are hereby incorporated herein in their entirety by reference.

TECHNICAL FIELD FOR THE INVENTION

The present invention relates to a convertible orthotic brace and especially to a flexible orthopedic brace providing for convenient adjustment to fit a wearer by adjustment to multiple configurations.

BACKGROUND OF THE INVENTION

Several prior art orthotic braces feature front and rear panels to provide lumbar support to the patient.

For instance, in U.S. Pat. Nos. 6,478,759 and 5,967,998, hereby incorporated herein by reference, a single front support panel is attached to one or more rear panels to provide lumbar support to the patient upon closure. Devices of this type provide better support in comparison to belt-type devices. These devices may feature a reinforcement insert, typically of relatively rigid plastic, inserted into a soft material rear portion which in turn is connected to a front portion by straps.

Other braces of the prior art include those described in U.S. Pat. No. 4,202,327 having a number of straps for connecting right and left sections with the straps secured to the jacket with hook-and-loop strips. U.S. Pat. No. 4,508,110 describes a jacket-type orthoses that limits motion in the thoracic or lumbo-sacral areas and uses a rigid orthoses design that may be adjusted by a patient pulling on a plurality of laces, each attached to a short strap having hook-and-loop material thereon which is used to attach the straps to predetermined positions on the rigid brace members. Other prior art U.S. patents for orthoses include U.S. Pat. No. 4,475,543, for a lumbo-sacral brace using an elastic belt fastened with a pouch in combination with a semi-wrap-around polyurethane foam splint cured in place in the pouch; U.S. Pat. No. 2,100,964, describing a surgical belt is illustrated in which a plurality of laces are interconnected to a single strap on either side thereof; and U.S. Pat. No. 3,926,183, disclosing a dorsal lumbo sacral support combines elastic and non-elastic straps in a support device for a person's back, thoracic or pelvic areas.

U.S. Pat. No. 3,927,665 relates to a lumbo-sacral support having an elastic body encircling band and inelastic tensioning system, while U.S. Pat. No. 5,074,288 illustrates a soft body brace attached to a patient with a plurality of straps to provide a back support system with interchangeable and positionally adjustable orthotic support.

U.S. Pat. No. 4,175,553 is also a lumbo-sacral orthosis orthopedic support for encircling the torso and has a plurality of straps, and U.S. Pat. No. 4,459,979 is an orthopedic appliance made of resilient material conforming to the lower back of a person and uses a plurality of adjustable straps.

U.S. Pat. No. 5,362,304 discloses a thoracic lumbar sacral orthosis device formed as a jacket and has support plates which can attach thereto, and U.S. Pat. No. 5,188,585 concerns a lumbo-sacral orthopedic support which encircles the torso of a patient and has adjustable strap portions. U.S. Pat. No. 4,559,933 describes an orthopedic lumbo-sacral corset using semi-rigid elements and inflatable pads.

The aforementioned patents are hereby incorporated herein by reference.

One of the problems with orthotic braces of the prior art is that they cannot be used as both a smaller lumbosacral belt ("LSB") type orthotic brace and as a relatively larger lumbosacral orthotic ("LSO") type brace.

Accordingly, it is desirable to provide an orthotic device that allows for the relatively convenient conversion between a smaller LSB type orthotic brace and as a relatively larger LSO type brace.

In addition, it is also desirable to provide an LSB-LSO convertible type orthotic brace with an improved supplementary sternal support for the upper thoracic area. Such supports of the prior art are designed with a ventral support rod extending from the frontal portion of the belt. This is relatively stiff and unyielding, and can feel confining for the wearer.

Accordingly, it is desirable to provide effective supplementary sternal support without relying upon a support that extends from the wearers front while providing equivalent supplementary sternal support.

In addition, it is normally inconvenient for wearers to be able to don and remove such a supplementary sternal support without disrupting the custom fitting of its attachment to the wearer. Thus, in this regard, it is also beneficial to provide such a supplementary sternal support that may be readily donned and removed by the wearer without the need to reposition the fitments that position the supplementary sternal support.

Accordingly, in light of the aforementioned shortcomings of currently available orthotic braces, there is a need for a convertible lumbar orthosis which can be adjusted on the patient so as to provide optional LSB- or LSO-type support while conforming to the back of a patient to provide a more customized fit.

In addition, there remains a need for LSO-type devices that permit the optional use of a supplementary sternal support without sacrificing comfort and ease of donning and removal while maintaining its customized fitting and support settings, such as by having to rearrange the straps of the brace.

SUMMARY OF THE INVENTION

In accordance with aspects of the present invention, a lumbar-sacral orthosis is provided comprising in combination a first lateral belt portion having a dorsal end portion having two substantially parallel horizontally extending upper and lower slots, and an inner surface bearing a pad, the first lateral belt portion having a third slot, a second lateral belt portion having a dorsal end portion having two substantially parallel horizontally extending upper and lower slots, and an inner surface bearing a pad, the first lateral belt portion substantially parallel horizontally extending upper and lower slots and the second lateral belt portion substantially parallel horizontally extending upper and lower slots being substantially aligned, a central dorsal portion, the central dorsal portion attached to the first and second lateral belt portions by an upper pin extending from the central dorsal portion through the upper slots, and a lower pin extending from the central dorsal portion through the lower slots, such that the first and second lateral belt portions may be moved with respect to one another, the central dorsal portion comprising, along its inner-facing surface, a rigid dorsal support panel, a first strap attached to the dorsal end portion of the second lateral belt portion by a first strap pin passing through the third slot, and a second strap attached to the dorsal end portion of the first lateral belt portion.

The first strap may comprise a first adjustment loop configured to adjust an extension length of the first strap relative to the second lateral belt portion. The second strap may comprise a second adjustment loop configured to adjust an extension length of the second strap relative to the first lateral belt portion. The first and second lateral belt portions may be adapted to overlap across the wearer's ventral area when the orthosis is donned. The dorsal support panel may be incorporated into the central dorsal portion such that it opens away from the wearer when the orthosis is donned. The lumbar-sacral orthosis may comprise a rigid ventral support panel, the first and second lateral belt portions being attached over the ventral support panel. The ventral support panel may comprise an upwardly extending sternal support portion. The sternal support portion may comprise at least two sternal straps connecting the sternal support portion and the dorsal support panel. The sternal straps of the sternal support portion may be adapted to extend under the wearer's arms. The sternal straps of the sternal support portion may be adapted to extend over the wearer's shoulders. The first strap and the second strap may be adapted to be releasably attached to the central dorsal portion. The dorsal support panel may comprise a polymer material. The ventral support panel may comprise a polymer material. The sternal support portion may comprise a polymer material.

In accordance further aspects of the present invention, a lumbar-sacral orthosis is provided comprising in combination a first lateral belt portion having a dorsal end portion, a second lateral belt portion having a dorsal end portion, a central dorsal portion, the central dorsal portion comprising, along its inner-facing surface, a rigid dorsal support panel, a first strap attached to the dorsal end portion of the second lateral belt portion by a first strap pin passing through the third slot, a second strap attached to the dorsal end portion of the first lateral belt portion, and a rigid ventral support panel, the first and second lateral belt portions being attached over the ventral support panel.

The ventral support panel may comprise an upwardly extending sternal support portion. The sternal support portion may comprise at least two sternal straps connecting the sternal support portion and the dorsal support panel. The sternal straps of the sternal support portion may be adapted to extend under the wearer's arms. The sternal straps of the sternal support portion may be adapted to extend over the wearer's shoulders. The dorsal end portion of the first lateral belt portion may comprise two substantially parallel horizontally extending upper and lower slots, and an inner surface bearing a pad, the first lateral belt portion having a third slot. The dorsal end portion of the second lateral belt portion may comprise two substantially parallel horizontally extending upper and lower slots, and an inner surface bearing a pad, the first lateral belt portion substantially parallel horizontally extending upper and lower slots and the second lateral belt portion substantially parallel horizontally extending upper and lower slots being substantially aligned. The central dorsal portion may be attached to the first and second lateral belt portions by an upper pin extending from the central dorsal portion through the upper slots, and a lower pin extending from the central dorsal portion through the lower slots, such that the first and second lateral belt portions may be moved with respect to one another.

In accordance with further aspects of the present invention, a lumbar-sacral orthosis is provided comprising in combination a first lateral belt portion having a dorsal end portion having two substantially parallel horizontally extending upper and lower slots, and an inner surface bearing a pad, the first lateral belt portion having a third slot, a second lateral belt portion having a dorsal end portion having two substantially parallel horizontally extending upper and lower slots, and an inner surface bearing a pad, the first lateral belt portion substantially parallel horizontally extending upper and lower slots and the second lateral belt portion substantially parallel horizontally extending upper and lower slots being substantially aligned, a central dorsal portion, the central dorsal portion attached to the first and second lateral belt portions by an upper pin extending from the central dorsal portion through the upper slots, and a lower pin extending from the central dorsal portion through the lower slots, such that the first and second lateral belt portions may be moved with respect to one another, the central dorsal portion comprising, along its inner-facing surface, a rigid dorsal support panel, the dorsal support panel attached to the first and second lateral belt portions by a right side dorsal pin and a left side dorsal pin, a first strap attached to the dorsal end portion of the second lateral belt portion by a first strap pin passing through the third slot, and a second strap attached to the dorsal end portion of the first lateral belt portion.

The first strap may comprise a first adjustment loop configured to adjust an extension length of the first strap relative to the second lateral belt portion. The second strap may comprise a second adjustment loop configured to adjust an extension length of the second strap relative to the first lateral belt portion. The first and second lateral belt portions may be adapted to overlap across the wearer's ventral area when the orthosis is donned. The dorsal support panel may be incorporated into the central dorsal portion such that it opens away from the wearer when the orthosis is donned. The lumbar-sacral orthosis may further comprise a rigid ventral support panel, the first and second lateral belt portions may be attached over the ventral support panel. The ventral support panel may comprise an upwardly extending sternal support portion. The sternal support portion may comprise at least two sternal straps connecting the sternal support portion and the dorsal support panel. The sternal straps of the sternal support portion may be adapted to extend under the wearer's arms. The sternal straps of the sternal support portion may be adapted to extend over the wearer's shoulders. The first strap and the second strap may be adapted to be releasably attached to the central dorsal portion. The dorsal support panel may comprise a polymer material. The ventral support panel may comprise a polymer material. The sternal support portion may comprise a polymer material.

In view of the foregoing summary and further detailed description, it will be appreciated that features of the present invention may be incorporated into an orthotic brace or belt to the extent not functionally inconsistent.

DETAILED DESCRIPTION OF THE PREFERRED EMBODIMENTS

In accordance with the foregoing summary of the invention, the following presents the preferred embodiments of the present invention, which are considered to be the best mode thereof.

Figure 1:
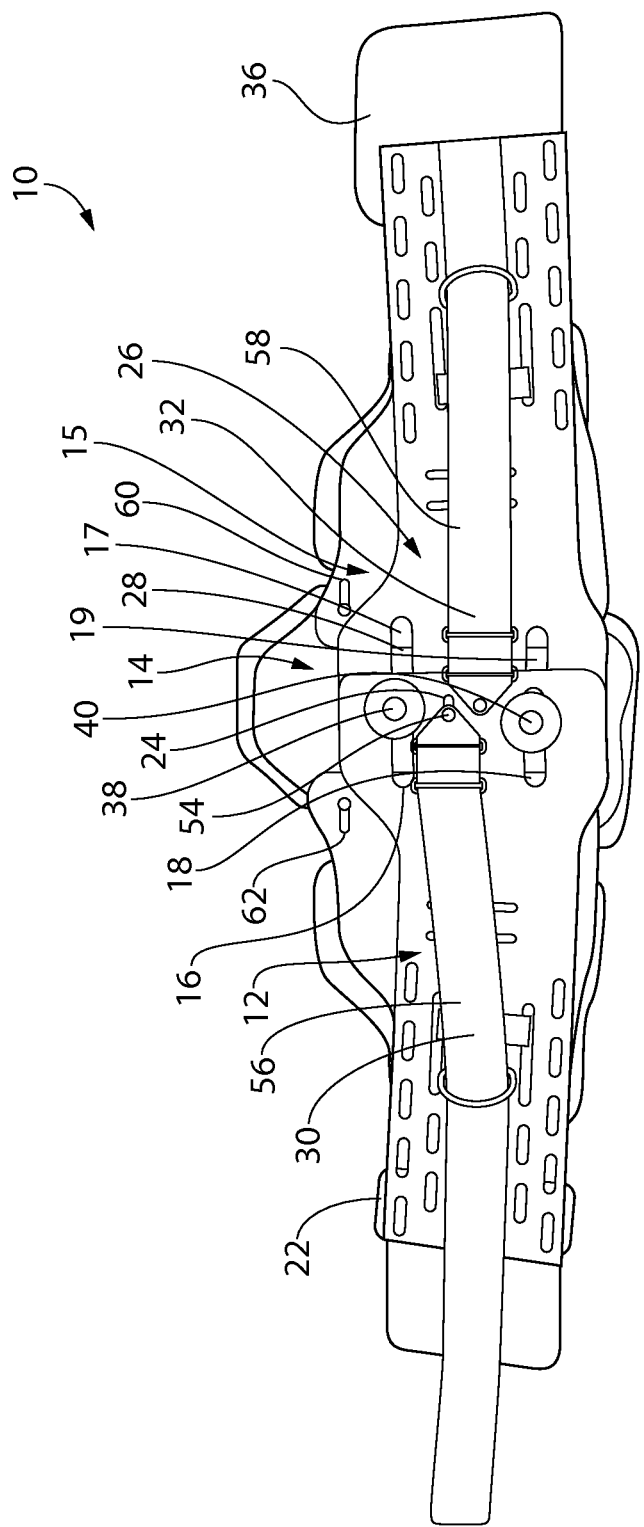
FIG. 1 is a rear plan view of an orthotic brace in an open position in accordance with aspects of the present invention.

Reference is now made to FIGS. 1-6, which show a preferred embodiment of an orthosis 10 of the present invention. FIG. 1 is a rear plan view of one embodiment of the present invention. The rear side of the orthotic brace of FIG. 1 is shown in an open position. The lumbar-sacral orthosis 10 includes a first lateral belt portion 12, a second lateral belt portion 26, a central dorsal portion 28, a first strap 30, and a second strap 32. The first lateral belt portion 12 has a dorsal end portion 14. The dorsal end portion 14 has a horizontally extending upper slot 16 and a horizontally extending lower slot 18. The two slots 16, 18 are substantially parallel, as shown in FIG. 1. The orthosis 10 further includes at least one inner surface 20 bearing at least one pad 22. The first lateral belt portion 12 includes a third slot 24. The second lateral belt portion 26 has a dorsal end portion 15 with a horizontally extending upper slot 17 and a horizontally extending lower slot 19, which are substantially parallel. The second lateral belt portion 26 includes at least one inner surface 34 bearing at least one pad 36. As shown in FIG. 1, the horizontally extending upper and lower slots 16, 18 of the first lateral belt portion 12 and the horizontally extending upper and lower slots 17, 19 of the second lateral belt portion 26 are substantially aligned.

Figure 3:
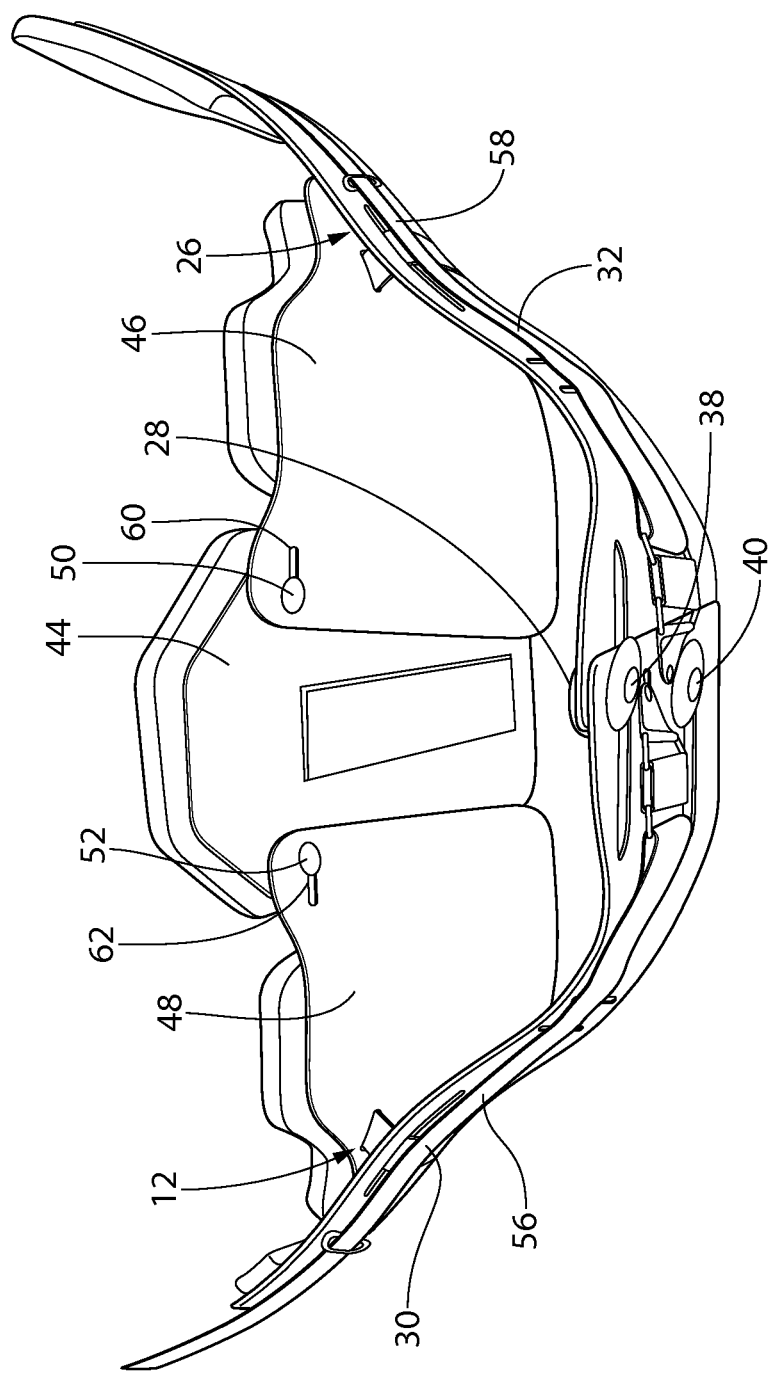
FIG. 3 is a top rear perspective view of an orthotic brace in an open position in accordance with further aspects of the present invention.
Figure 6:
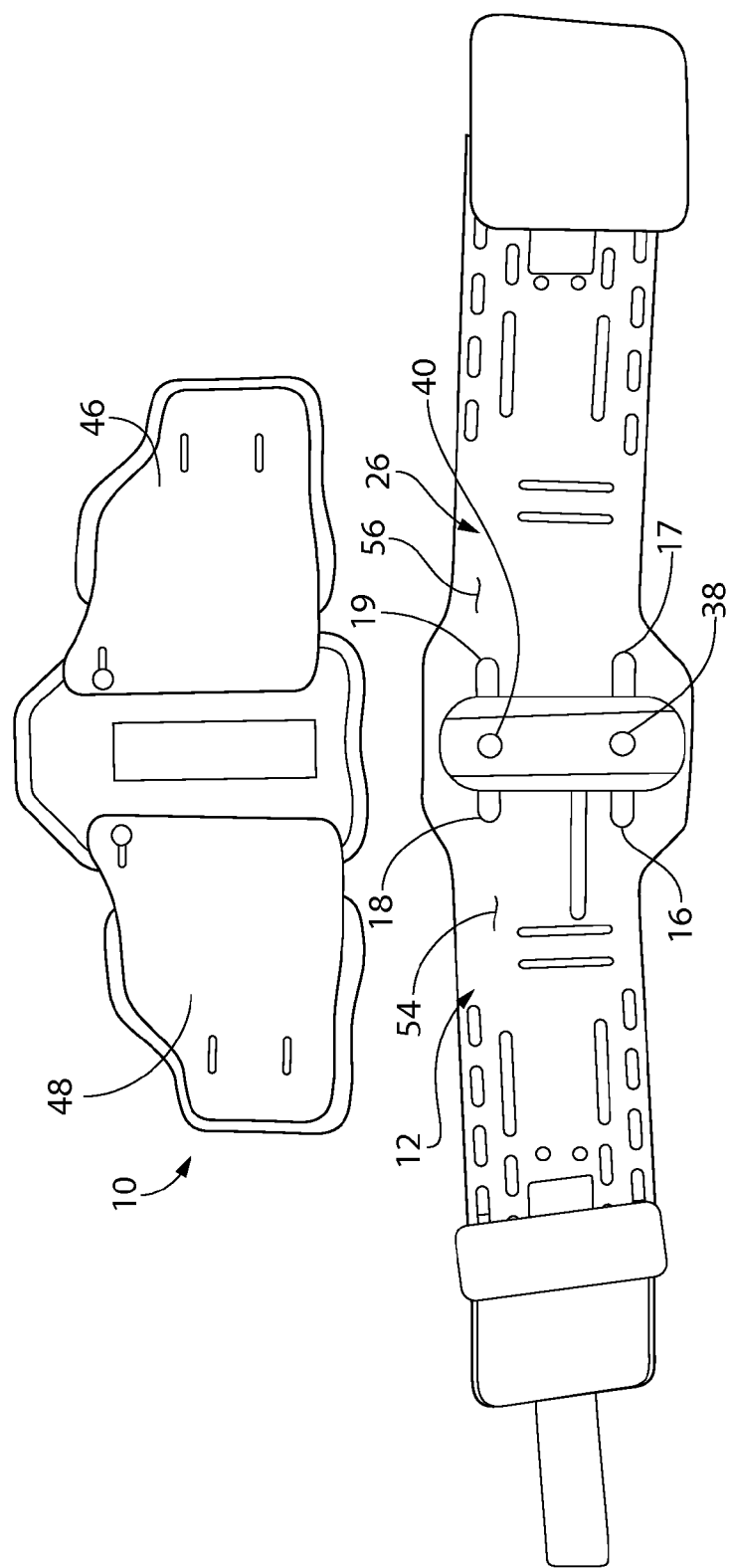
FIG. 6 is an exploded inside view of an orthotic brace in an open position in accordance with further aspects of the present invention.

Referring now to FIG. 6, the first and second lateral belt portions 12, 26 of the orthotic brace 10 of a preferred embodiment of the present invention include a right dorsal panel 46 and a left dorsal panel 48. The right and left side dorsal panels 46, 48 are shown as separate portions of the lateral belt portions 12, 26 attached at inside surfaces 54, 56 of the first and second lateral belt portions 12, 26 by hook-and-loop fastener straps through slots, as best shown in FIGS. 3 and 6. However, the right and left side dorsal panels 46, 48 may be integrally formed with the first and second lateral belt portions 12, 26.

Figure 2:
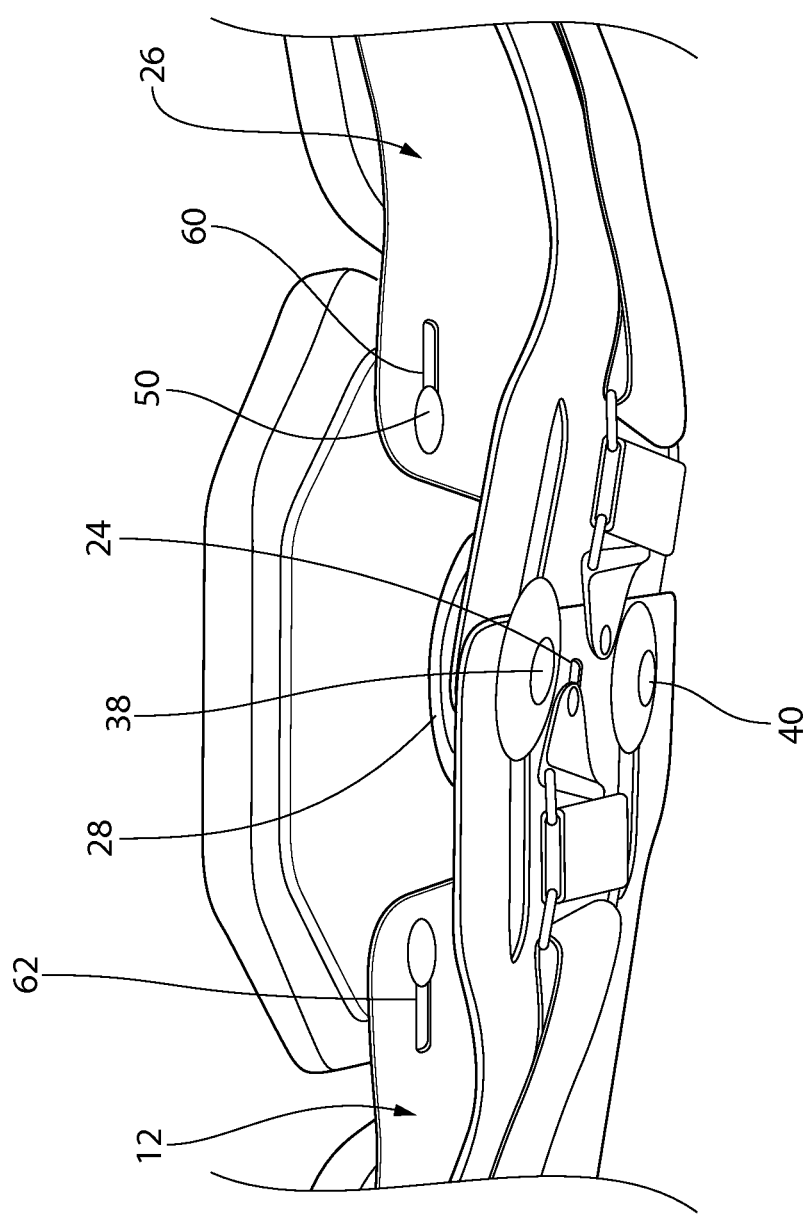
FIG. 2 is a top plan view of an orthotic brace in an open position in accordance with further aspects of the present invention.

Reference is now made to FIG. 2, which shows the central dorsal portion 28 attached to the first and second lateral belt portions 12, 26 by an upper pin 38 extending from the central dorsal portion 28 through the upper slots 16, 17, and a lower pin 40 extending from the central dorsal portion 28 through the lower slots 18, 19. This arrangement allows the first and second lateral belt portions 12, 26 to be moved with respect to one another.

Figure 4:
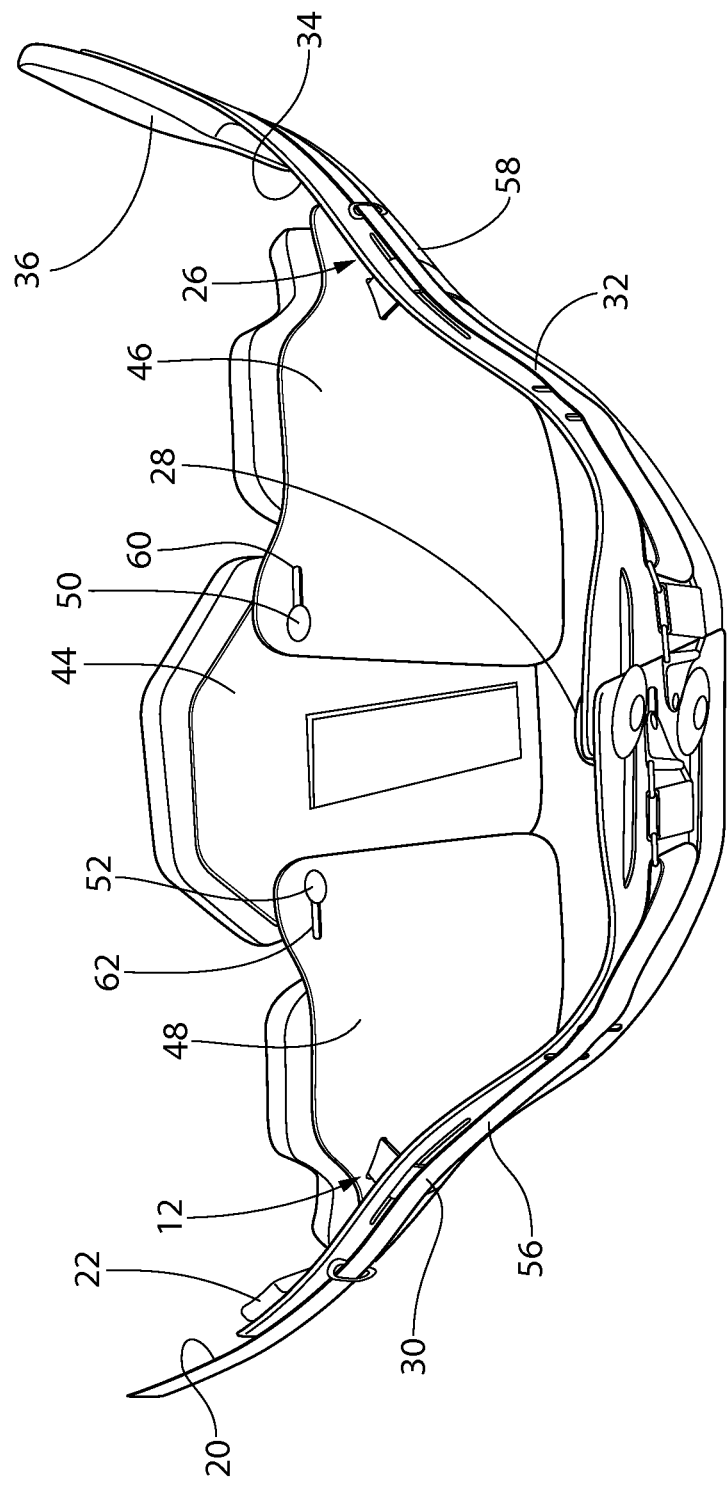
FIG. 4 is an exploded top view of an orthotic brace in an open position in accordance with further aspects of the present invention.

Referring now to FIGS. 3 and 4, the central dorsal portion 28 includes, along an inner-facing surface 42, a rigid dorsal support panel 44. The dorsal support panel 44 is attached to the right dorsal panel 46 and the left dorsal panel 48 of the first and second lateral belt portions 12, 26 by a right side dorsal pin 50 and a left side dorsal pin 52. The right side dorsal pin 50 is fixed to the dorsal support panel 44 and moves in a right side dorsal slot 60 in the right dorsal panel 46. Similarly, the left side dorsal pin 52 is fixed to the dorsal support panel 44 and moves in a left side dorsal slot 62 in the left dorsal panel 48.

Referring again to FIGS. 1 and 2, the first strap 30 is attached to the dorsal end portion 15 of the second lateral belt portion 26 by a first strap pin 54 passing through the third slot 24. A second strap 32 is attached to the dorsal end portion 14 of the first lateral belt portion 12. The first strap 30, as shown in FIG. 1, includes a first adjustment loop 56 configured to adjust an extension length of the first strap 30 relative to the second lateral belt portion 26. The second strap 32, as shown in FIG. 1, has a second adjustment loop 58 configured to adjust an extension length of the second strap 32 relative to the first lateral belt portion 12. The first and second lateral belt portions 12, 26 are adapted to overlap across a wearer's ventral area when the orthosis 10 is donned. The dorsal support panel 44 is incorporated into the central dorsal portion 28 such that it opens away from the wearer when the orthosis 10 is donned.

In the embodiment shown in FIGS. 1-6, the first and second lateral belt portion 12, 26, the central dorsal portion 28, the dorsal support panel 44, and the left and right dorsal panels 46, 48 comprise a polymer material.

Figure 5:
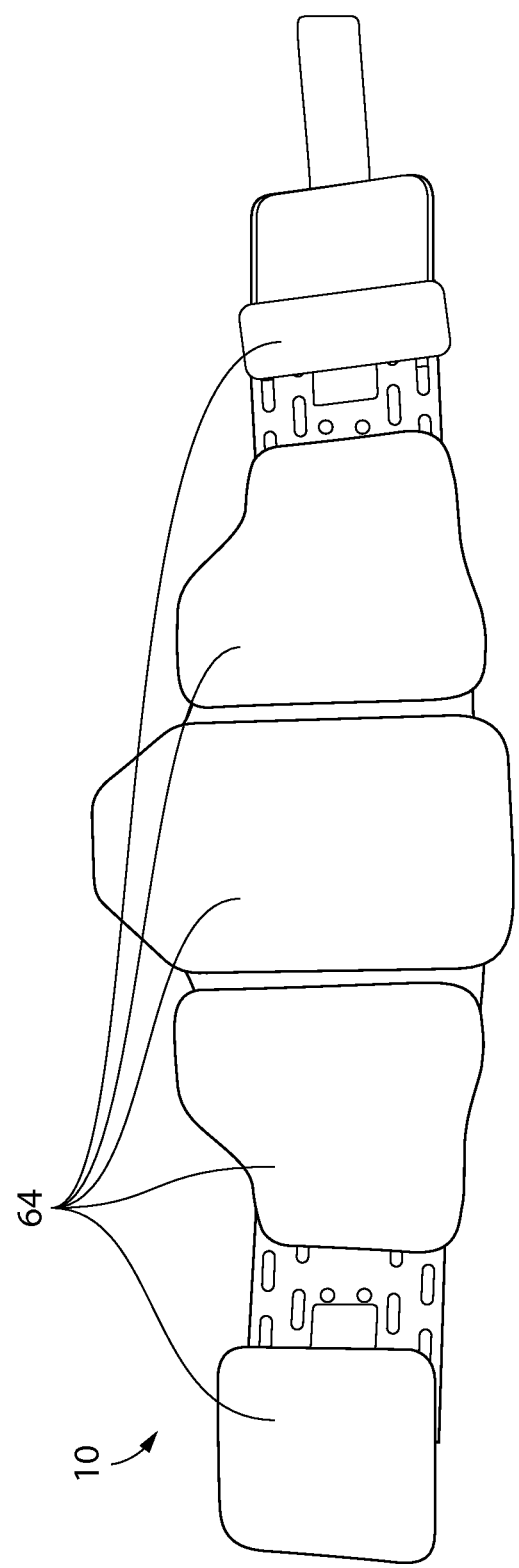
FIG. 5 is a front plan view of an orthotic brace in an open position in accordance with further aspects of the present invention.

Referring now to FIG. 5, each polymer portion or panel of the orthosis 10 may include one or more pads 64 at an inner side in order to increase comfort and support for the wearer.

Figure 7:
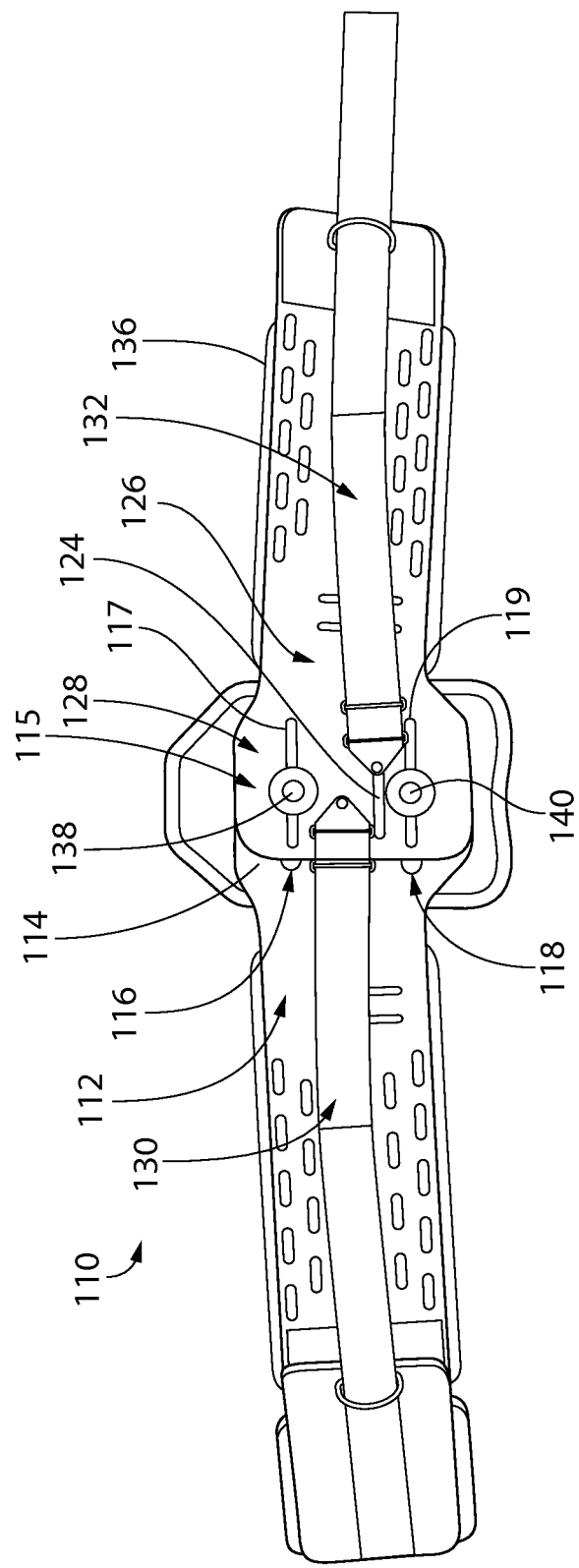
FIG. 7 is a rear plan view of an orthotic brace in an open position in accordance with further aspects of the present invention.

Reference is now made to FIGS. 7-11, which shows a preferred embodiment of the present invention. Referring to FIG. 7, a rear side view of a lumbar-sacral orthosis 110 is shown comprising a first lateral belt portion 112, a second lateral belt portion 126, a central dorsal portion 128, a first strap 130, and a second strap 132. The first lateral belt portion 112 has a dorsal end portion 114 having two substantially parallel horizontally extending upper and lower slots 116, 118, and an inner surface 120 bearing a pad 122. The second lateral belt portion 126 has a third slot 124. The second lateral belt portion 126 has a dorsal end portion 115 with two substantially parallel horizontally extending upper and lower slots 117, 119, and an inner surface 134 bearing a pad 136. The first lateral belt portion substantially parallel horizontally extending upper and lower slots 116, 118 and the second lateral belt portion substantially parallel horizontally extending upper and lower slots 117, 119 are substantially aligned. The central dorsal portion 128 is attached to the first and second lateral belt portions 112, 126 by an upper pin 138 extending from the central dorsal portion 128 through the upper slots 116, 117, and a lower pin 140 extending from the central dorsal portion 128 through the lower slots 118, 119, such that the first and second lateral belt portions 112, 126 may be moved with respect to one another.

Figure 8:
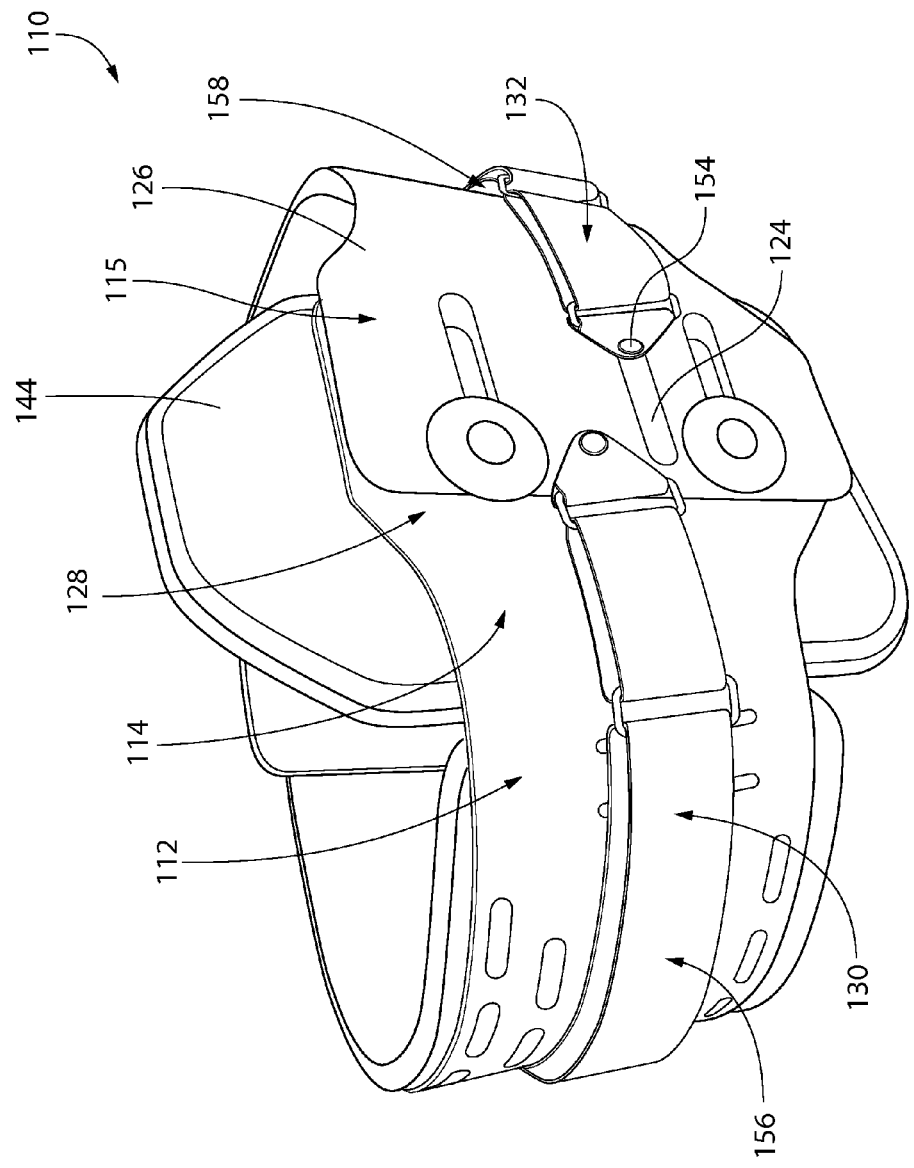
FIG. 8 is a rear left perspective view of an orthotic brace in a closed position in accordance with further aspects of the present invention.

Referring now to FIG. 8, the central dorsal portion 128 has, along an inner-facing surface, a rigid dorsal support panel 144. The second strap 132 is attached to the dorsal end portion 114 of the first lateral belt portion 112 by a first strap pin 154 passing through the third slot 124. The first strap 130 is attached to the dorsal end portion 115 of the second lateral belt portion 126. The first strap 130 of the preferred embodiment shown in FIGS. 7-11 comprises a first adjustment loop 156 configured to adjust an extension length of the first strap 130 relative to the second lateral belt portion 126. The second strap 132 of the preferred embodiment comprises a second adjustment loop 158 configured to adjust an extension length of the second strap 132 relative to the first lateral belt portion 112.

Figure 9:
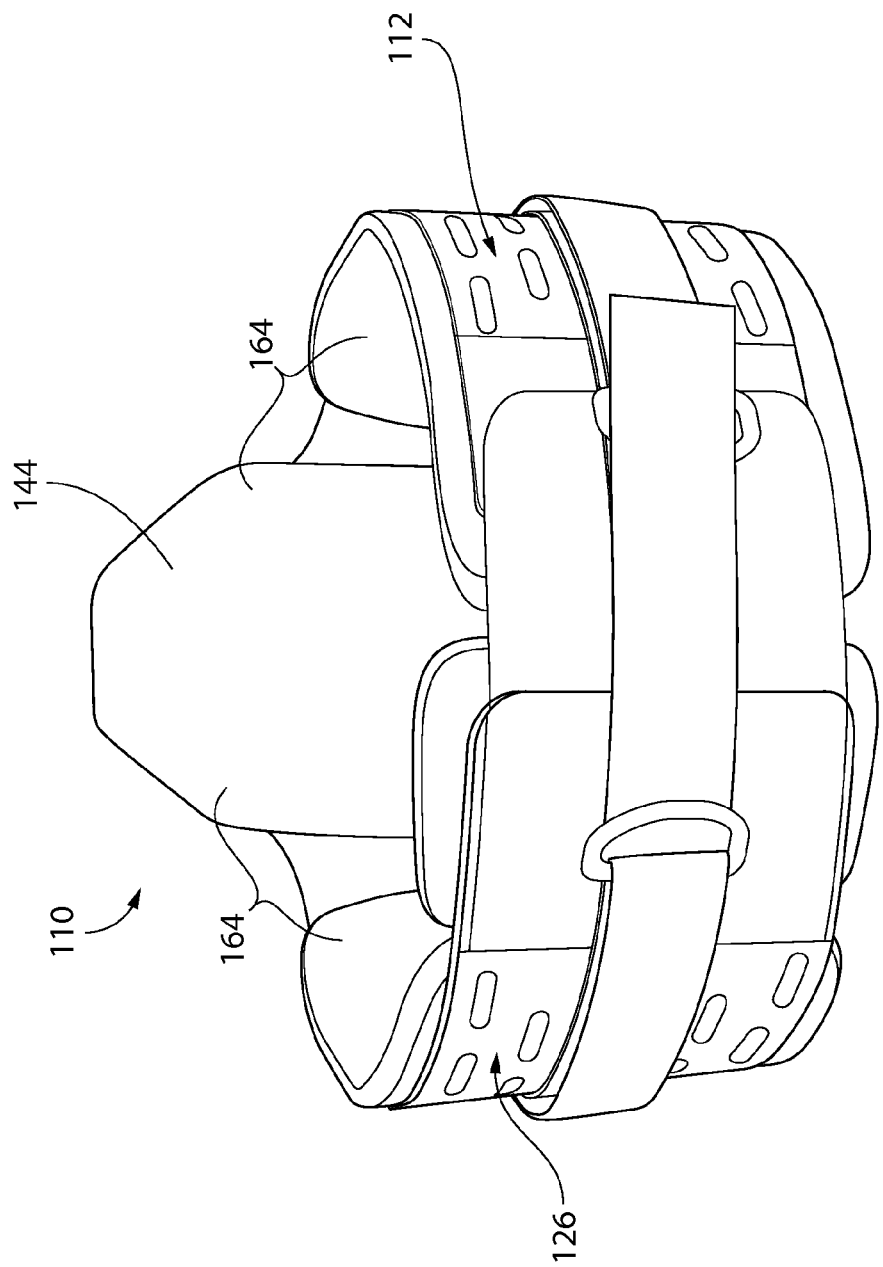
FIG. 9 is a front perspective view of an orthotic brace in a closed position in accordance with further aspects of the present invention.

Referring now to FIG. 9, the first and second lateral belt portions 112, 126 are adapted to overlap across the wearer's ventral area when the orthosis 110 is donned. As can be recognized in FIGS. 7-9, the dorsal support panel 144 is incorporated into the central dorsal portion 138 such that it opens away from the wearer when the orthosis 110 is donned.

In the embodiment shown in FIGS. 7-11, the first and second lateral belt portion 112, 126, the central dorsal portion 128, and the dorsal support panel 144 comprise a polymer material. Further, each polymer portion or panel of the orthosis 110 may include one or more pads 164 at an inner side in order to increase comfort and support for the wearer.

Figure 10:
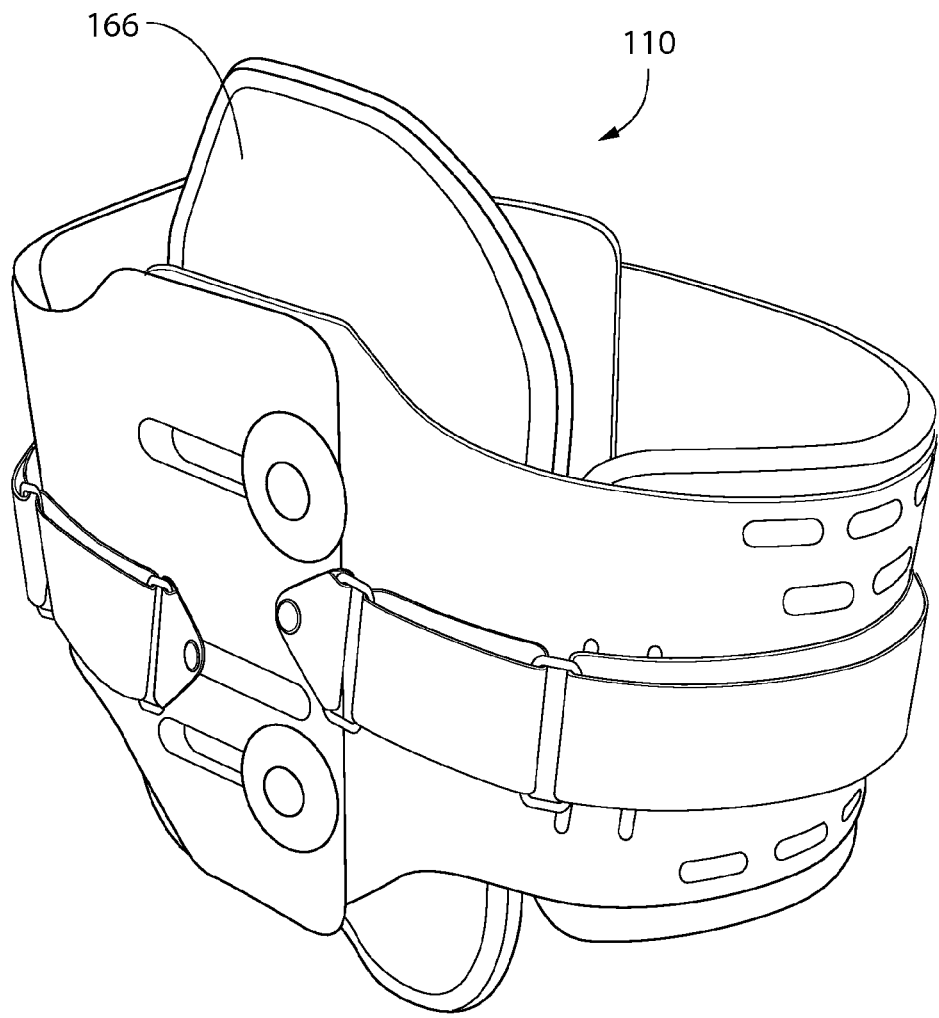
FIG. 10 is a rear right perspective view of an orthotic brace in a closed position in accordance with further aspects of the present invention.
Figure 11:
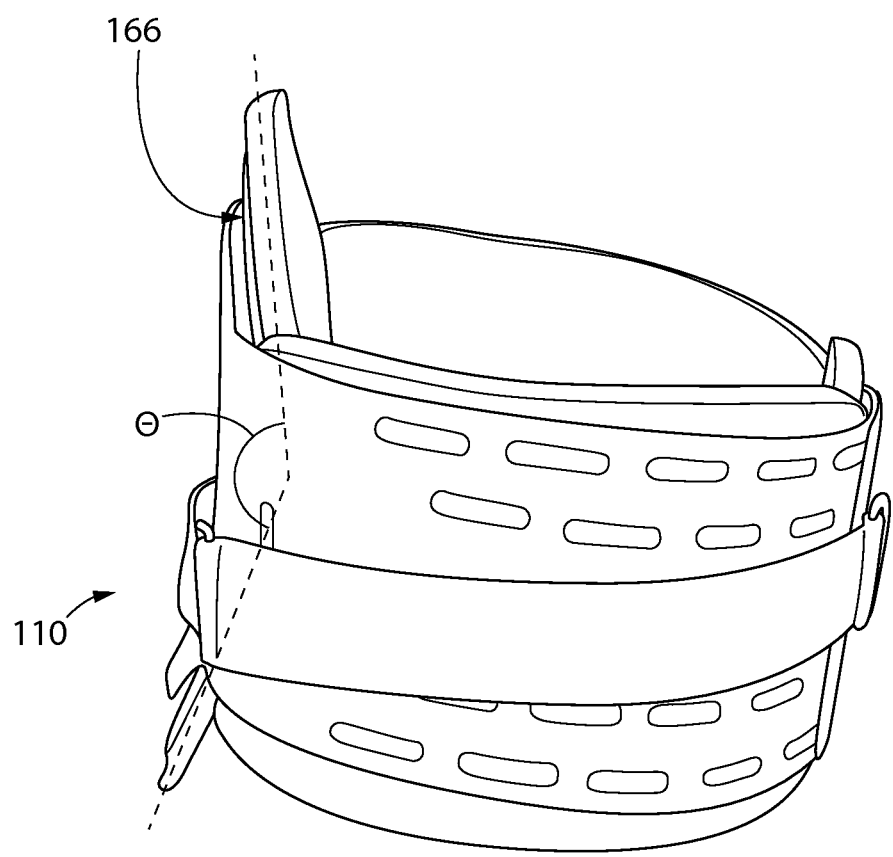
FIG. 11 is a right perspective view of an orthotic brace in a closed position in accordance with further aspects of the present invention.
Figure 12:
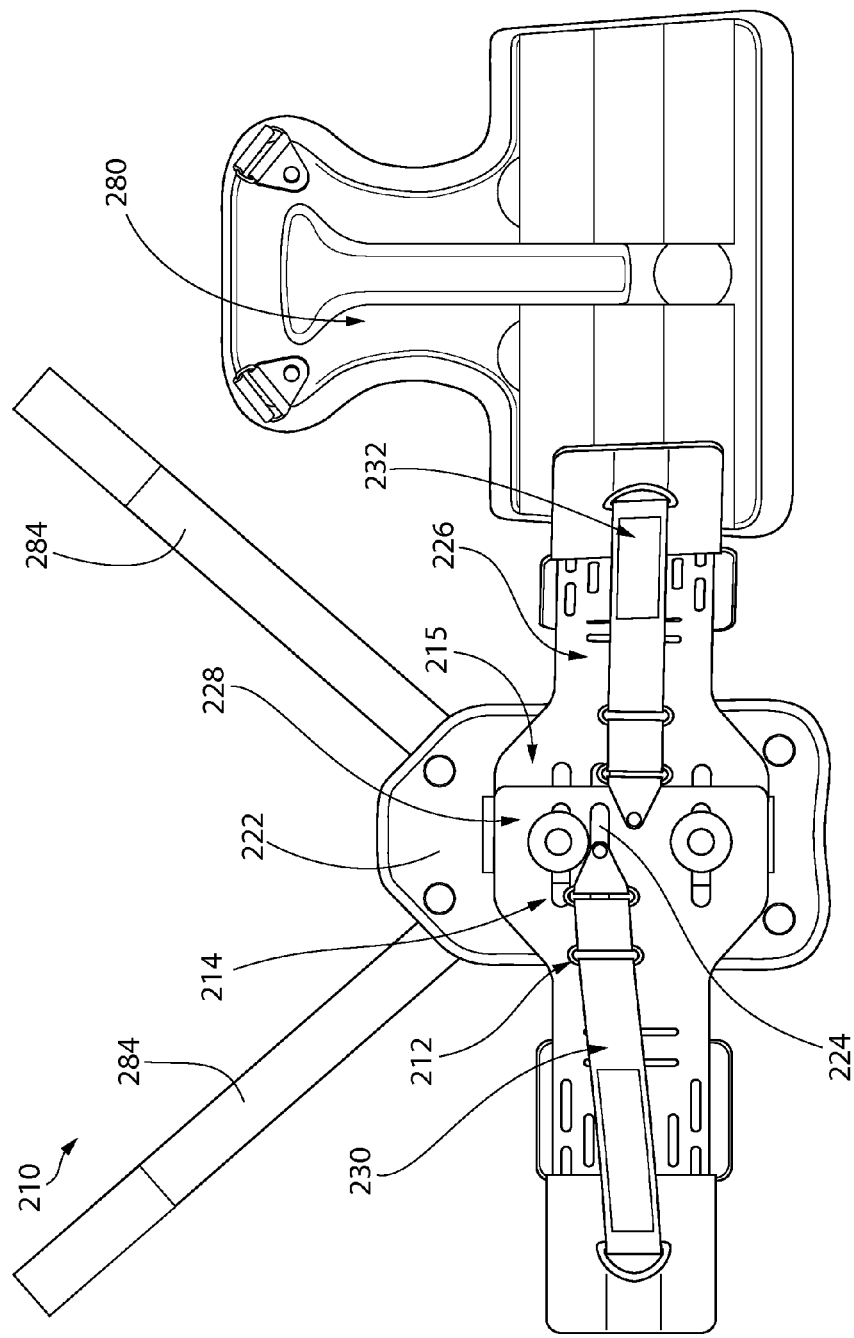
FIG. 12 is a front plan view of an orthotic brace in an open position in accordance with further aspects of the present invention.
Figure 13:
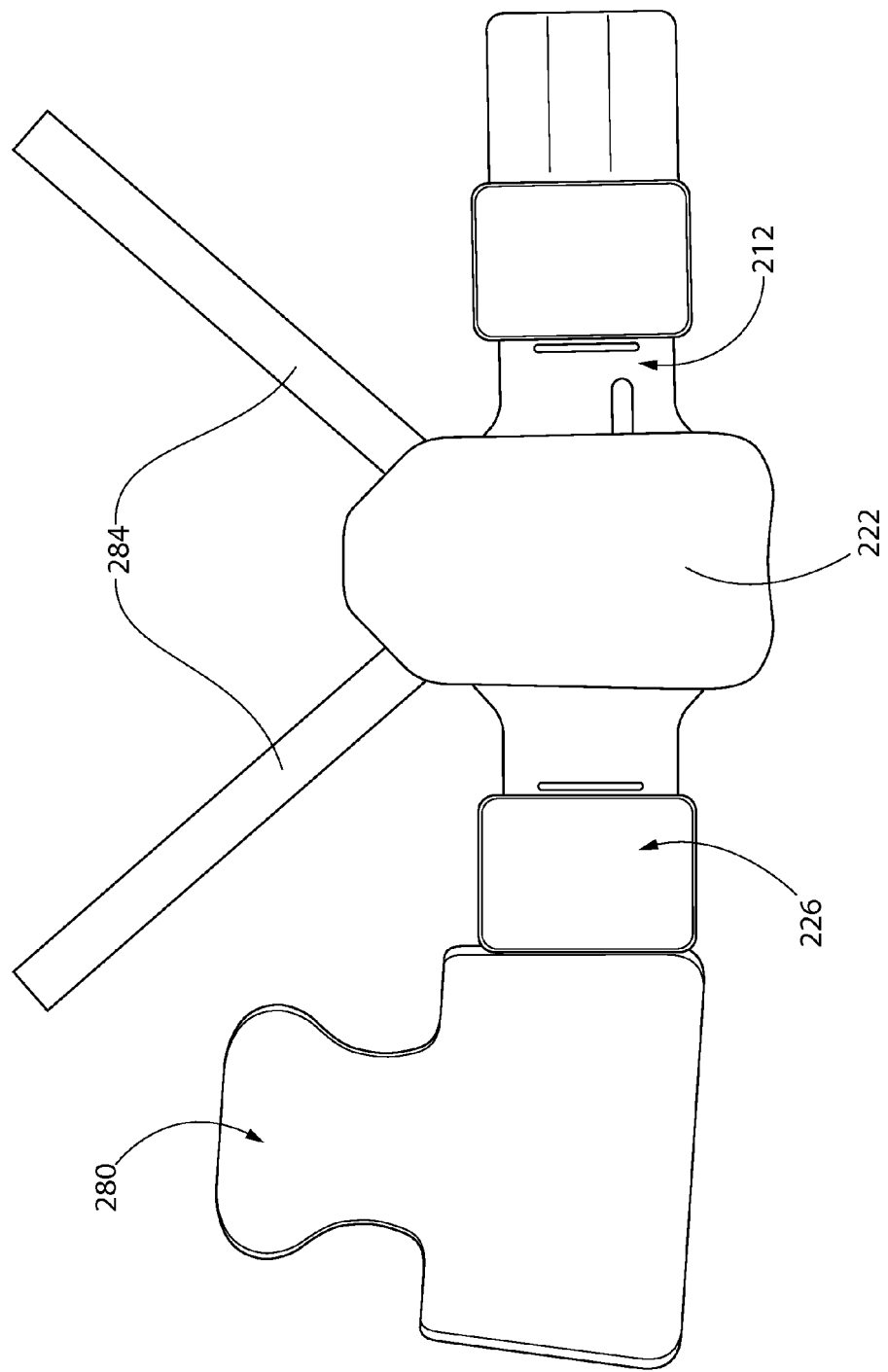
FIG. 13 is a rear plan view of an orthotic brace in an open position in accordance with further aspects of the present invention.

Referring now to FIGS. 10 and 11, the orthosis 110 may include a dorsal support panel 166 that is curved, as shown most clearly in FIG. 11. The dorsal support panel 166 may be curved or shaped in a plurality of configurations in order to provide custom support for the lumbar region of the wearer. Further, any dorsal support panel of any embodiment of the present invention may be straight or curved like the dorsal support panel 166 shown in FIGS. 10 and 11. The dorsal support panel 166 shown in FIGS. 10 and 11 shows how the dorsal support panel 166 is bent at an angle theta (8). The dorsal support panel 166 of the preferred embodiment has an angle theta in the range of 10-30 degrees, preferably 15-25 degrees, and most preferably 18 to 23 degrees.

Figure 14:
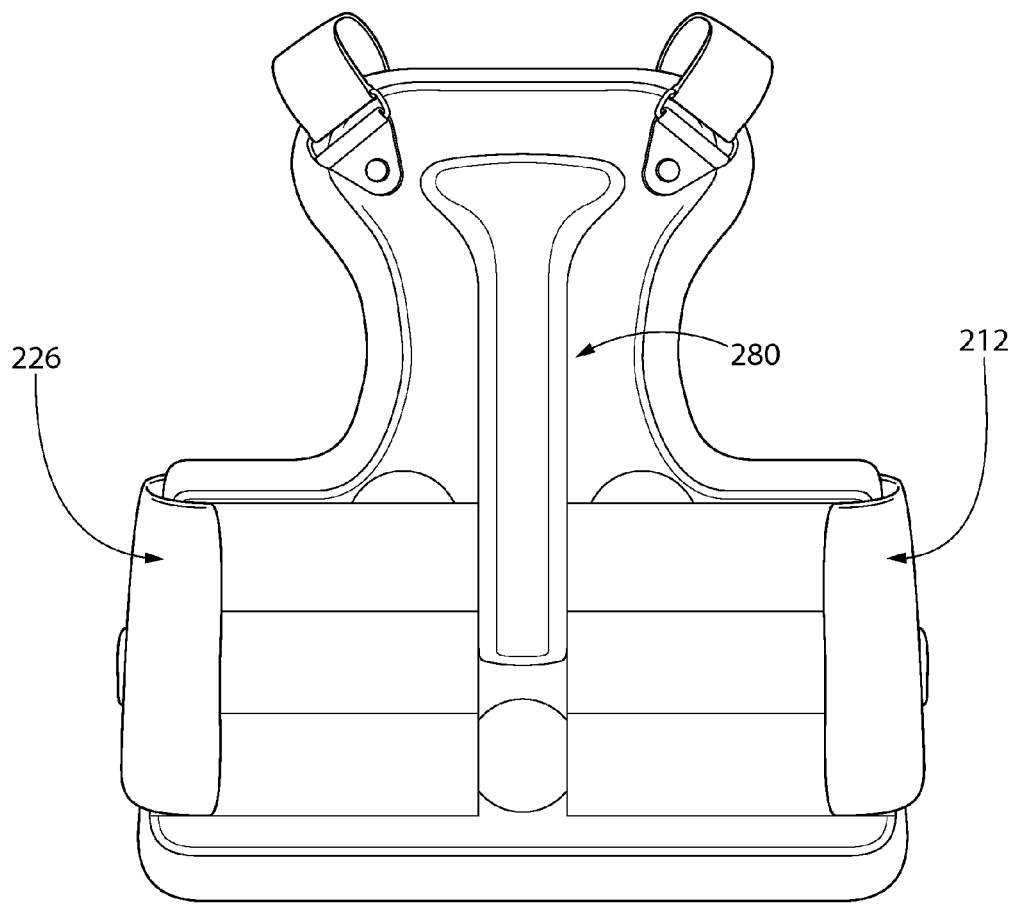
FIG. 14 is a front perspective view of an orthotic brace in a closed position in accordance with further aspects of the present invention.
Figure 15:
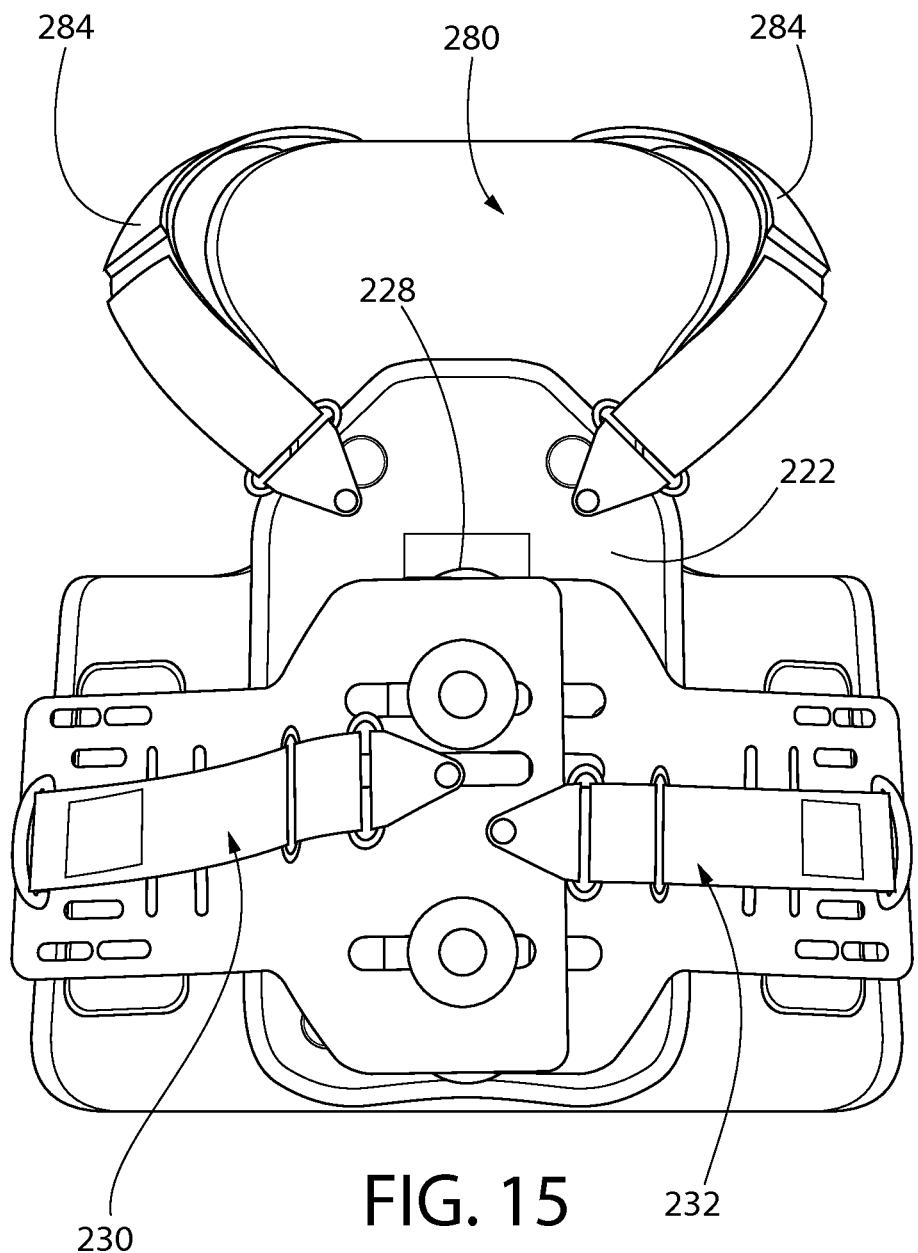
FIG. 15 is a rear perspective view of an orthotic brace in a closed position in accordance with further aspects of the present invention.
Figure 16:
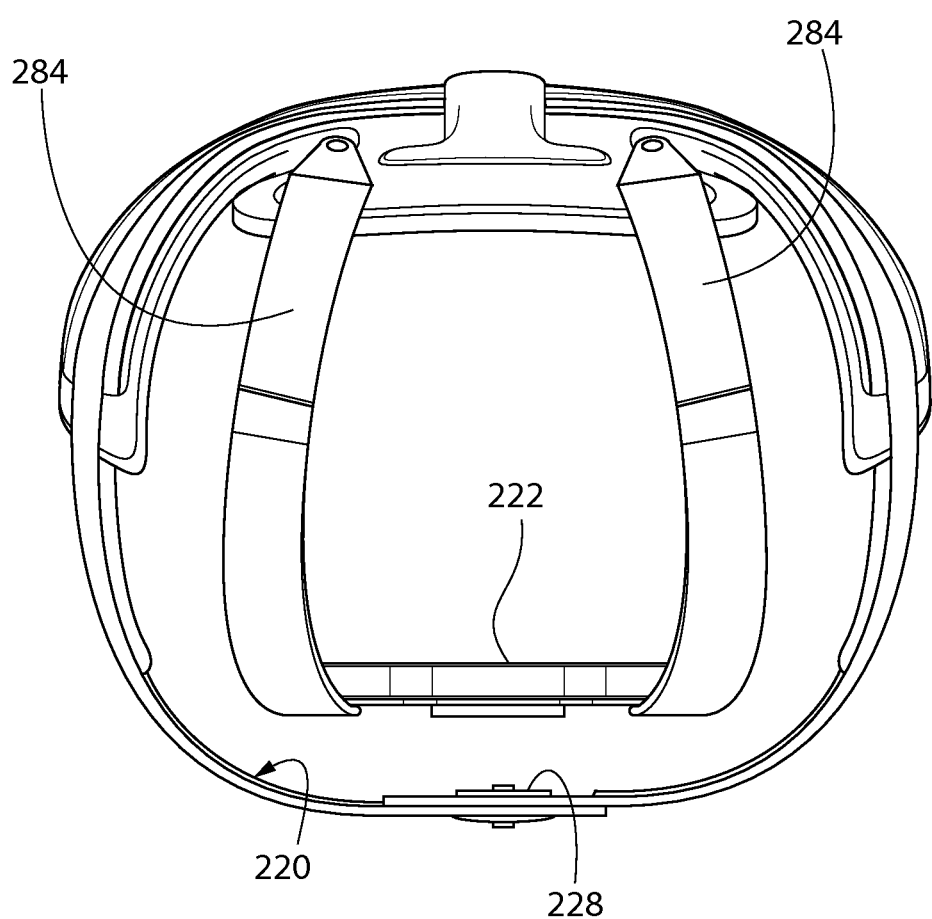
FIG. 16 is an exploded top view of an orthotic brace in a closed position in accordance with further aspects of the present invention.

Reference is now made to FIGS. 12-21, which show a preferred embodiment of an orthosis 210 of the present invention. The lumbar-sacral orthosis 210 comprises a first lateral belt portion 212, a second lateral belt portion 226, a central dorsal portion 228, a first strap 230, a second strap 232, and a rigid ventral support panel 280. The first lateral belt portion 212 includes a dorsal end portion 214 and the second lateral belt portion 226 has a dorsal end portion 215. The central dorsal portion 228 comprises, along its inner-facing surface 220, a rigid dorsal support panel 222. The first strap 230 is attached to the dorsal end portion 215 of the second lateral belt portion 226 by a first strap pin passing through a third slot 224. The second strap 232 is attached to the dorsal end portion 214 of the first lateral belt portion 212. The first and second lateral belt portions 212, 226 are attached over the ventral support panel 280, as best shown in FIG. 14.

Figure 17:
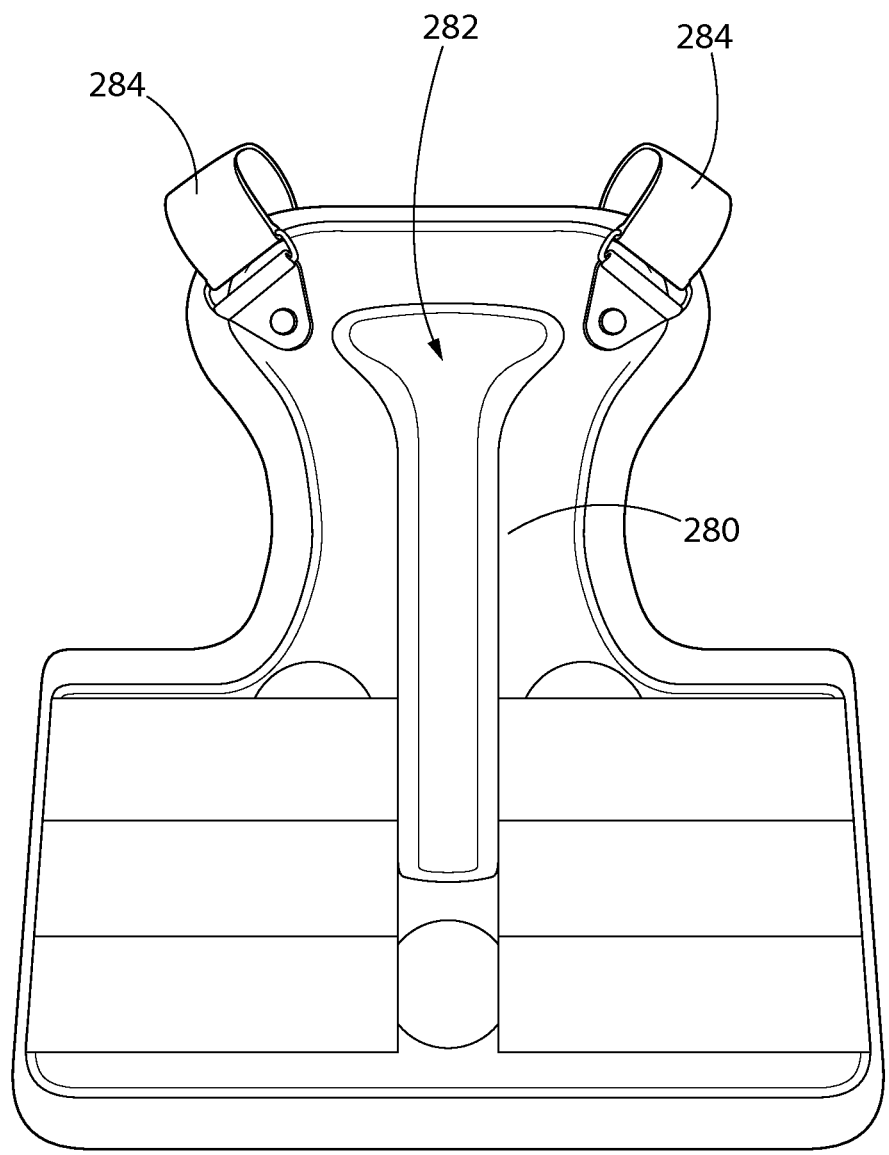
FIG. 17 is a front perspective view of a partial orthotic brace in accordance with further aspects of the present invention.
Figure 18:
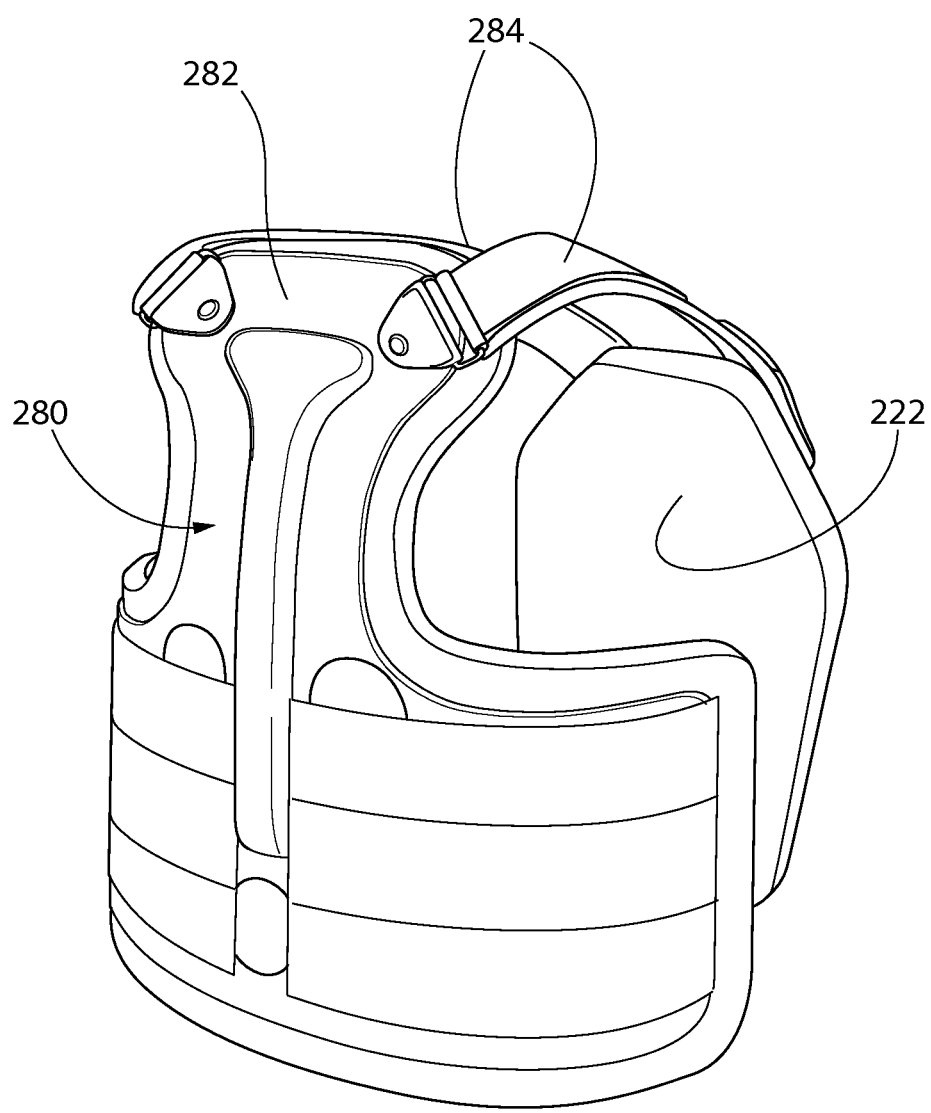
FIG. 18 is a front left perspective view of a partial orthotic brace in accordance with further aspects of the present invention.
Figure 19:
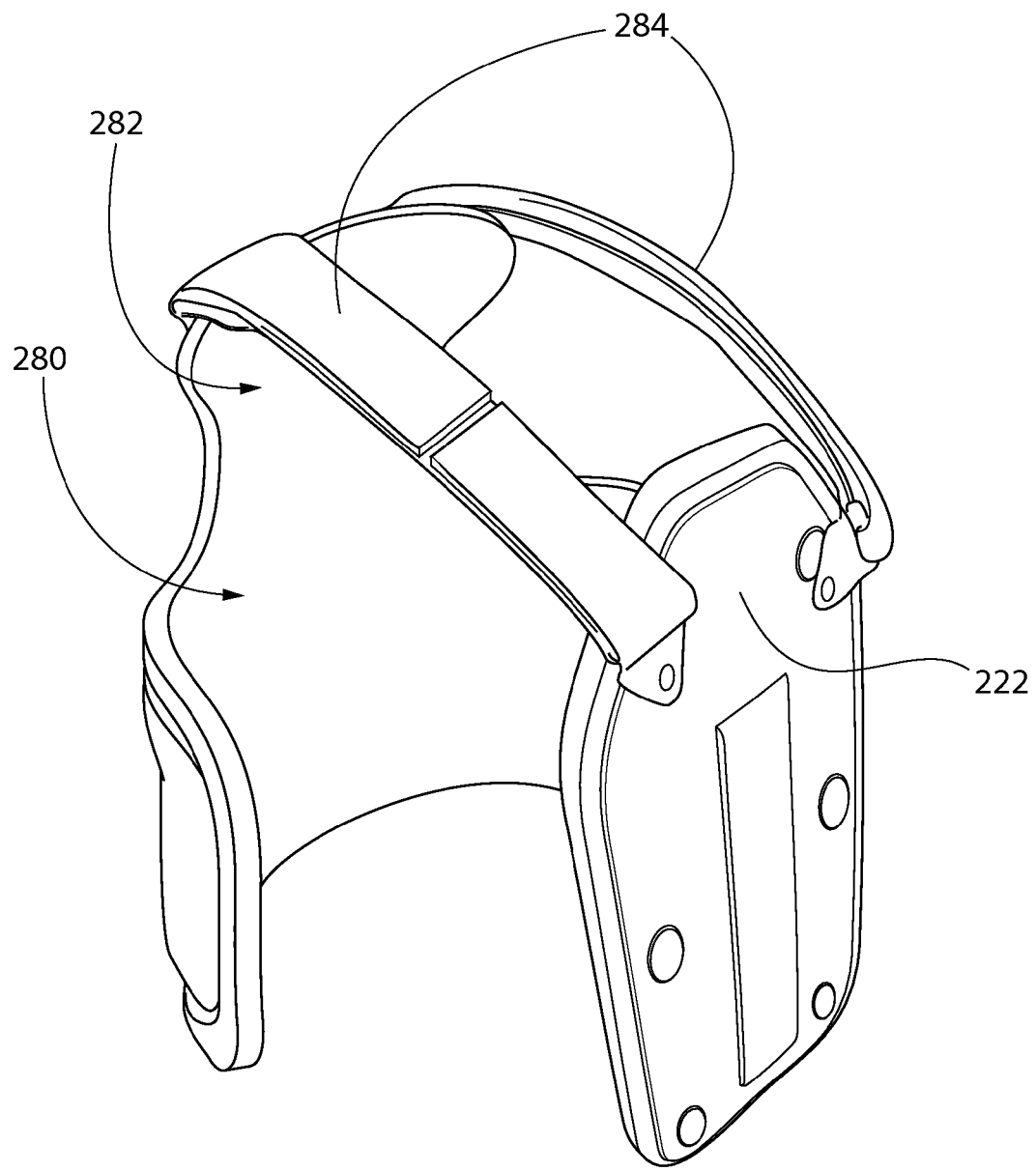
FIG. 19 is a rear left perspective view of a partial orthotic brace in accordance with further aspects of the present invention.

Referring now to FIGS. 17-19, the ventral support panel 280 of the preferred embodiment of the present invention includes an upwardly extending sternal support portion 282. The sternal support portion 282 has at least two sternal straps 284 connecting the sternal support portion 282 and the dorsal support panel 222. As can be recognized by the embodiment shown in FIG. 18, the sternal straps 284 of the sternal support portion 282 may be adapted to extend either over the wearer's shoulders or under the wearer's arms.

Figure 20:
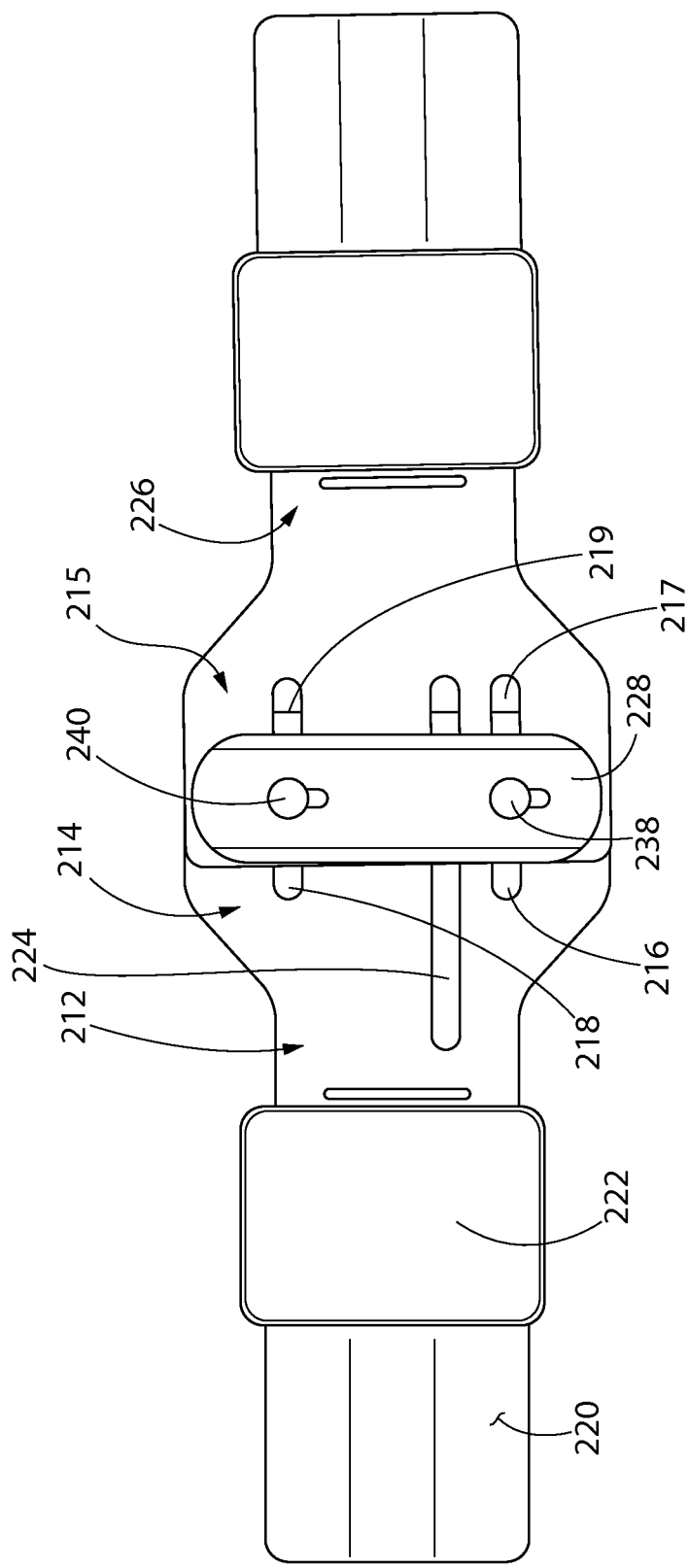
FIG. 20 is a front plan view of a partial orthotic brace in accordance with further aspects of the present invention.
Figure 21:
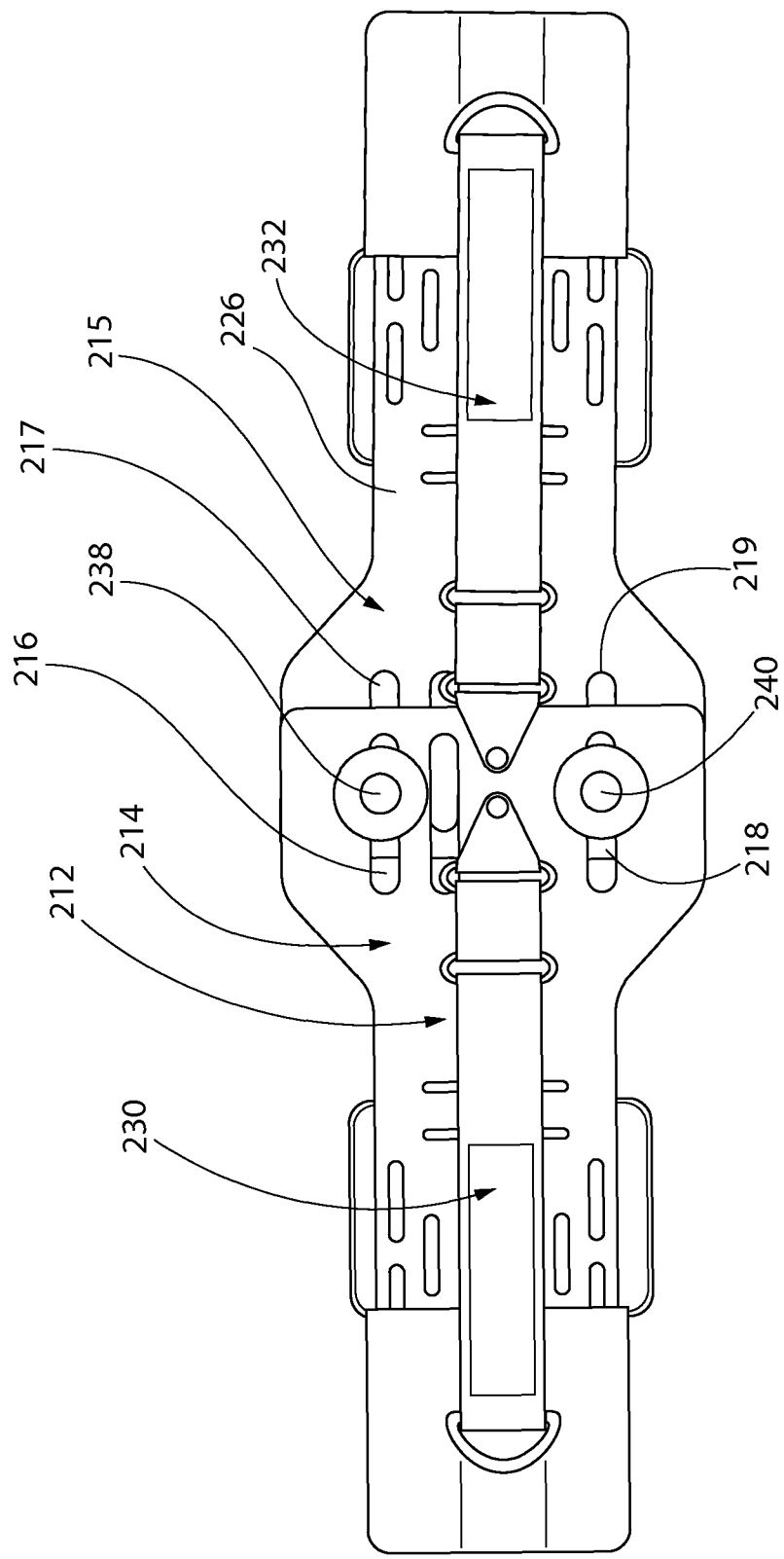
FIG. 21 is a rear plan view of a partial orthotic brace in accordance with further aspects of the present invention.

Referring now to FIGS. 20 and 21, the dorsal end portion 214 of the first lateral belt portion 212 and the dorsal end portion 215 of the second lateral belt portion 126 are shown without the ventral support panel 280. The dorsal end portion 214 has two substantially parallel horizontally extending upper and lower slots 216, 218, and an inner surface 220 bearing a pad 222. The first lateral belt portion 212 has a third slot 224. The dorsal end portion 215 of the second lateral belt portion 226 includes two substantially parallel horizontally extending upper and lower slots 217, 219, and an inner surface 234 bearing a pad 236. The first lateral belt portion substantially parallel horizontally extending upper and lower slots 216, 218 and the second lateral belt portion substantially parallel horizontally extending upper and lower slots 217, 219 are substantially aligned. The central dorsal portion 228 is attached to the first and second lateral belt portions 212, 226 by an upper pin 238 extending from the central dorsal portion 228 through the upper slots 216, 217, and a lower pin 240 extending from the central dorsal portion 228 through the lower slots 218, 219, such that the first and second lateral belt portions 212, 216 may be moved with respect to one another.

The support panels and portions may be made of any dimensionally stable material, typically rigid enough to provide reinforcement to the lumbar portion of the brace, such as in reinforcement inserts known and used in the art, such as through use of a polymeric material. In a preferred embodiment, and as a non-limiting example, the support panels and portions may be made of any dimensionally stable material such as ABS plastic of at least one-eighth inch in thickness.

The optional inner pads, such as pads 22, 122, and 222, may be constructed of any appropriate cloth or foam material (or combination thereof). This is known and used in the orthotic brace field.

From FIGS. 1-21, one can appreciate how the brace is closed either by the overlapping of the first and second lateral belt portions and cinching of the first and second lateral belt portions by action of straps which are pulled toward the front of the belt using D-rings, or by attaching the first and second lateral belt portions to a ventral support panel then pulling the straps toward the front of the belt. The inner surfaces of straps are provided with hook-and-loop closure materials which attach to the outside of one or both of the lateral belt portions, to a ventral support panel, or to a hook-and-loop panel as shown in the Figures.

To don the orthotic device 10, 110, 210, the wearer will hold the device and support it as the ventral support panel is positioned approximately in front of the wearer's stomach area. With the ventral support panel in position, first and second lateral belt portions are arranged in overlapping relationship such that the hook-and-loop panels engage one another or the ventral support panel. The wearer then grasps the D rings of the straps and pulls the straps outwardly and forward such that the first and second lateral belt portions cinch with respect to one another across the wearer's back. The wearer then attaches the front strap ends to the lateral belt portions or the ventral support panel.

While the invention may be rendered in embodiments in many different forms, there have been shown in the drawings and described herein, in detail, the preferred embodiments of the present invention. It should be understood, however, that the present disclosure is to be considered an exemplification of the principles of the invention and is not intended to limit the spirit or scope of the invention and/or claims of the embodiments illustrated.

What is claimed is:

1. A lumbar-sacral orthosis comprising in combination:
   a. a first lateral belt portion having a dorsal end portion having two substantially parallel horizontally extending upper and lower slots, and an inner surface bearing a pad, said first lateral belt portion having a third slot;
   b. a second lateral belt portion having a dorsal end portion having two substantially parallel horizontally extending upper and lower slots, and an inner surface bearing a pad, said first lateral belt portion substantially parallel horizontally extending upper and lower slots and said second lateral belt portion substantially parallel horizontally extending upper and lower slots being substantially aligned;
   c. a central dorsal portion, said central dorsal portion attached to said first and second lateral belt portions by an upper pin extending from said central dorsal portion through said upper slots, and a lower pin extending from said central dorsal portion through said lower slots, such that said first and second lateral belt portions may be moved with respect to one another; said central dorsal portion comprising, along its inner-facing surface, a rigid dorsal support panel;
   d. a first strap attached to said dorsal end portion of said second lateral belt portion by a first strap pin passing through said third slot; and
   e. a second strap attached to said dorsal end portion of said first lateral belt portion.

2. The lumbar-sacral orthosis according to claim 1 wherein said first strap comprises a first adjustment loop configured to adjust an extension length of said first strap relative to said second lateral belt portion.

3. The lumbar-sacral orthosis according to claim 1 wherein said second strap comprises a second adjustment loop configured to adjust an extension length of said second strap relative to said first lateral belt portion.

4. The lumbar-sacral orthosis according to claim 1 wherein said first and second lateral belt portions are adapted to overlap across the wearer's ventral area when said orthosis is donned.

5. The lumbar-sacral orthosis according to claim 1 wherein said dorsal support panel is incorporated into said central dorsal portion such that it opens away from the wearer when said orthosis is donned.

6. The lumbar-sacral orthosis according to claim 1 further comprising a rigid ventral support panel, said first and second lateral belt portions being attached over said ventral support panel.

7. The lumbar-sacral orthosis according to claim 6 wherein said ventral support panel comprises an upwardly extending sternal support portion.

8. The lumbar-sacral orthosis according to claim 7 wherein said sternal support portion comprises at least two sternal straps connecting said sternal support portion and said dorsal support panel.

9. The lumbar-sacral orthosis according to claim 8 wherein said sternal straps of said sternal support portion are adapted to extend under the wearer's arms.

10. The lumbar-sacral orthosis according to claim 8 wherein said sternal straps of said sternal support portion are adapted to extend over the wearer's shoulders.

11. A lumbar-sacral orthosis according to claim 1 wherein said first strap and said second strap are adapted to be releasably attached to said central dorsal portion.

12. A lumbo-sacral orthopedic brace in accordance with claim 1 wherein said dorsal support panel comprises a polymer material.

13. A lumbo-sacral orthopedic brace in accordance with claim 1 wherein said ventral support panel comprises a polymer material.

14. A lumbo-sacral orthopedic brace in accordance with claim 1 wherein said sternal support portion comprises a polymer material.

15. A lumbar-sacral orthosis comprising in combination:
   a. a first lateral belt portion having a dorsal end portion and a third slot;
   b. a second lateral belt portion having a dorsal end portion;
   c. a central dorsal portion, said central dorsal portion comprising, along its inner-facing surface, a rigid dorsal support panel;
   d. a first strap attached to said dorsal end portion of said second lateral belt portion by a first strap pin passing through said third slot;
   e. a second strap attached to said dorsal end portion of said first lateral belt portion; and
   f. a rigid ventral support panel, said first and second lateral belt portions being attached over said ventral support panel.

16. The lumbar-sacral orthosis according to claim 15 wherein said ventral support panel comprises an upwardly extending sternal support portion.

17. The lumbar-sacral orthosis according to claim 16 wherein said sternal support portion comprises at least two sternal straps connecting said sternal support portion and said dorsal support panel.

18. The lumbar-sacral orthosis according to claim 17 wherein said sternal straps of said sternal support portion are adapted to extend under the wearer's arms.

19. The lumbar-sacral orthosis according to claim 17 wherein said sternal straps of said sternal support portion are adapted to extend over the wearer's shoulders.

20. The lumbar-sacral orthosis according to claim 15 wherein said dorsal end portion of said first lateral belt portion comprises two substantially parallel horizontally extending upper and lower slots, and an inner surface bearing a pad, said first lateral belt portion having a third slot.

21. The lumbar-sacral orthosis according to claim 20 wherein said dorsal end portion of said second lateral belt portion comprises two substantially parallel horizontally extending upper and lower slots, and an inner surface bearing a pad, said first lateral belt portion substantially parallel horizontally extending upper and lower slots and said second lateral belt portion substantially parallel horizontally extending upper and lower slots being substantially aligned.

22. The lumbar-sacral orthosis according to claim 21 wherein said central dorsal portion is attached to said first and second lateral belt portions by an upper pin extending from said central dorsal portion through said upper slots, and a lower pin extending from said central dorsal portion through said lower slots, such that said first and second lateral belt portions may be moved with respect to one another.

23. A lumbar-sacral orthosis comprising in combination:
   a. a first lateral belt portion having a dorsal end portion having two substantially parallel horizontally extending upper and lower slots, and an inner surface bearing a pad, said first lateral belt portion having a third slot;
   b. a second lateral belt portion having a dorsal end portion having two substantially parallel horizontally extending upper and lower slots, and an inner surface bearing a pad, said first lateral belt portion substantially parallel horizontally extending upper and lower slots and said second lateral belt portion substantially parallel horizontally extending upper and lower slots being substantially aligned;
   c. a central dorsal portion, said central dorsal portion attached to said first and second lateral belt portions by an upper pin extending from said central dorsal portion through said upper slots, and a lower pin extending from said central dorsal portion through said lower slots, such that said first and second lateral belt portions may be moved with respect to one another; said central dorsal portion comprising, along its inner-facing surface, a rigid dorsal support panel, said dorsal support panel attached to said first and second lateral belt portions by a right side dorsal pin and a left side dorsal pin;
   d. a first strap attached to said dorsal end portion of said second lateral belt portion by a first strap pin passing through said third slot; and
   e. a second strap attached to said dorsal end portion of said first lateral belt portion.

24. The lumbar-sacral orthosis according to claim 23 wherein said first strap comprises a first adjustment loop configured to adjust an extension length of said first strap relative to said second lateral belt portion.

25. The lumbar-sacral orthosis according to claim 23 wherein said second strap comprises a second adjustment loop configured to adjust an extension length of said second strap relative to said first lateral belt portion.

26. The lumbar-sacral orthosis according to claim 23 wherein said first and second lateral belt portions are adapted to overlap across the wearer's ventral area when said orthosis is donned.

27. The lumbar-sacral orthosis according to claim 23 wherein said dorsal support panel is incorporated into said central dorsal portion such that it opens away from the wearer when said orthosis is donned.

28. The lumbar-sacral orthosis according to claim 23 further comprising a rigid ventral support panel, said first and second lateral belt portions being attached over said ventral support panel.

29. The lumbar-sacral orthosis according to claim 28 wherein said ventral support panel comprises an upwardly extending sternal support portion.

30. The lumbar-sacral orthosis according to claim 29 wherein said sternal support portion comprises at least two sternal straps connecting said sternal support portion and said dorsal support panel.

31. The lumbar-sacral orthosis according to claim 30 wherein said sternal straps of said sternal support portion are adapted to extend under the wearer's arms.

32. The lumbar-sacral orthosis according to claim 30 wherein said sternal straps of said sternal support portion are adapted to extend over the wearer's shoulders.

33. A lumbar-sacral orthosis according to claim 23 wherein said first strap and said second strap are adapted to be releasably attached to said central dorsal portion.

34. A lumbo-sacral orthopedic brace in accordance with claim 23 wherein said dorsal support panel comprises a polymer material.

35. A lumbo-sacral orthopedic brace in accordance with claim 23 wherein said ventral support panel comprises a polymer material.

36. A lumbo-sacral orthopedic brace in accordance with claim 23 wherein said sternal support portion comprises a polymer material.

* * * * *